United States Patent
Hong et al.

(10) Patent No.: US 9,890,468 B2
(45) Date of Patent: Feb. 13, 2018

(54) METHOD OF MAKING A BREATH SENSING TUBE

(71) Applicant: National Tsing Hua University, Hsinchu (TW)

(72) Inventors: Chien-Chong Hong, Zhubei (TW); Kuan-Wen Chen, Taichung (TW); Wei-Han Wang, Xiluo Township (TW); Chung-Hsuan Wu, Tainan (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 259 days.

(21) Appl. No.: 14/735,969

(22) Filed: Jun. 10, 2015

(65) Prior Publication Data
US 2016/0160373 A1 Jun. 9, 2016

(30) Foreign Application Priority Data
Dec. 8, 2014 (TW) .............................. 103142602 A

(51) Int. Cl.
| C25D 15/00 | (2006.01) |
| C25D 13/22 | (2006.01) |
| C25D 13/14 | (2006.01) |
| G01N 33/497 | (2006.01) |
| C25D 13/02 | (2006.01) |
| C25D 13/18 | (2006.01) |

(52) U.S. Cl.
CPC .............. *C25D 13/22* (2013.01); *C25D 13/02* (2013.01); *C25D 13/14* (2013.01); *C25D 13/18* (2013.01); *C25D 15/00* (2013.01); *G01N 33/497* (2013.01)

(58) Field of Classification Search
CPC ...... G01N 33/497; C25D 13/12; C25D 13/14; C25D 13/16; C25D 13/22; C25D 15/00
See application file for complete search history.

(56) References Cited

U.S. PATENT DOCUMENTS

| 7,968,474 B2* | 6/2011 | Martin ...................... B82B 3/00 257/E21.536 |
| 2004/0211271 A1 | 10/2004 | Han et al. |
| 2012/0104361 A1 | 5/2012 | Hsu |
| 2012/0135158 A1* | 5/2012 | Freer ...................... B82Y 10/00 427/532 |

FOREIGN PATENT DOCUMENTS

| TW | 201003057 A | 1/2010 |
| TW | 201218378 A1 | 5/2012 |

* cited by examiner

*Primary Examiner* — Justin Olamit
(74) *Attorney, Agent, or Firm* — Birch, Stewart, Kolasch & Birch, LLP

(57) ABSTRACT

A method of making a breath sensing tube includes: (A) dispersing a nanowire material in a solution in a dielectriphoretic bath, such that the nanowire material is formed into individual nanowires and nanowire aggregates; (B) adsorbing the nanowire aggregates on a bath electrode through dielectrophoresis so as to obtain a nanowire-containing solution containing the individual nanowires; contacting sensor electrodes of a substrate with the nanowire-containing solution; and subjecting the nanowire-containing solution to dielectrophoresis, so that one of the individual nanowires is adsorbed to the sensor electrodes to interconnect the sensor electrodes.

6 Claims, 17 Drawing Sheets

METHOD OF MAKING A BREATH SENSING TUBE

CROSS-REFERENCE TO RELATED APPLICATION

This application claims priority of Taiwanese Application No. 103142602, filed on Dec. 8, 2014.

FIELD

The disclosure relates to a method of making a breath sensing tube, more particularly to a method of making a breath sensing tube that includes a single nanowire interconnecting two sensor electrodes.

BACKGROUND

An Exhaled Breath Condensate (EBC) system is a conventional breath detection system for collecting and detecting a breath gas.

The Exhaled Breath Condensate system is configured to continuously collect and condense a breath gas which is exhaled by a tester through a condenser so as to obtain a collected breath condensate. The collected breath condensate system is analyzed by a gas analysis equipment.

An advantage of the Exhaled Breath Condensate system is that it is portable. However, the Exhaled Breath Condensate system is disadvantageous in that it takes a lot of time to condense the breath gas.

SUMMARY

Therefore, an object of the disclosure is to provide a method of making a breath sensing tube that can alleviate at least one of the drawbacks of the prior arts.

According to the disclosure, a method of making a breath sensing tube includes: (A) dispersing a nanowire material in a solution in a dielectrophoretic bath, such that the nanowire material is formed into a plurality of individual nanowires and a plurality of nanowire aggregates in the solution in the dielectrophoretic bath; (B) adsorbing the nanowire aggregates on a bath electrode of the dielectrophoretic bath through dielectrophoresis so as to obtain a nanowire-containing solution containing the individual nanowires; (C) providing a substrate formed with at least one pair of sensor electrodes thereon; (D) contacting the sensor electrodes with the nanowire-containing solution; and (E) subjecting the nanowire-containing solution to dielectrophoresis, so that one of the individual nanowiresis is adsorbed to the sensor electrodes to interconnect the sensor electrodes.

Another object of the disclosure is to provide a breath sensing tube.

According to the disclosure, a breath sensing tube includes: a blowing body defining a blowing channel; a patterned circuit layer including two sensor electrodes which are disposed in the blowing channel and which are spaces apart from each other, each of the sensor electrodes has a tapered end portion with a tip; and a single nanowire interconnecting the tips of the tapered end portions.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
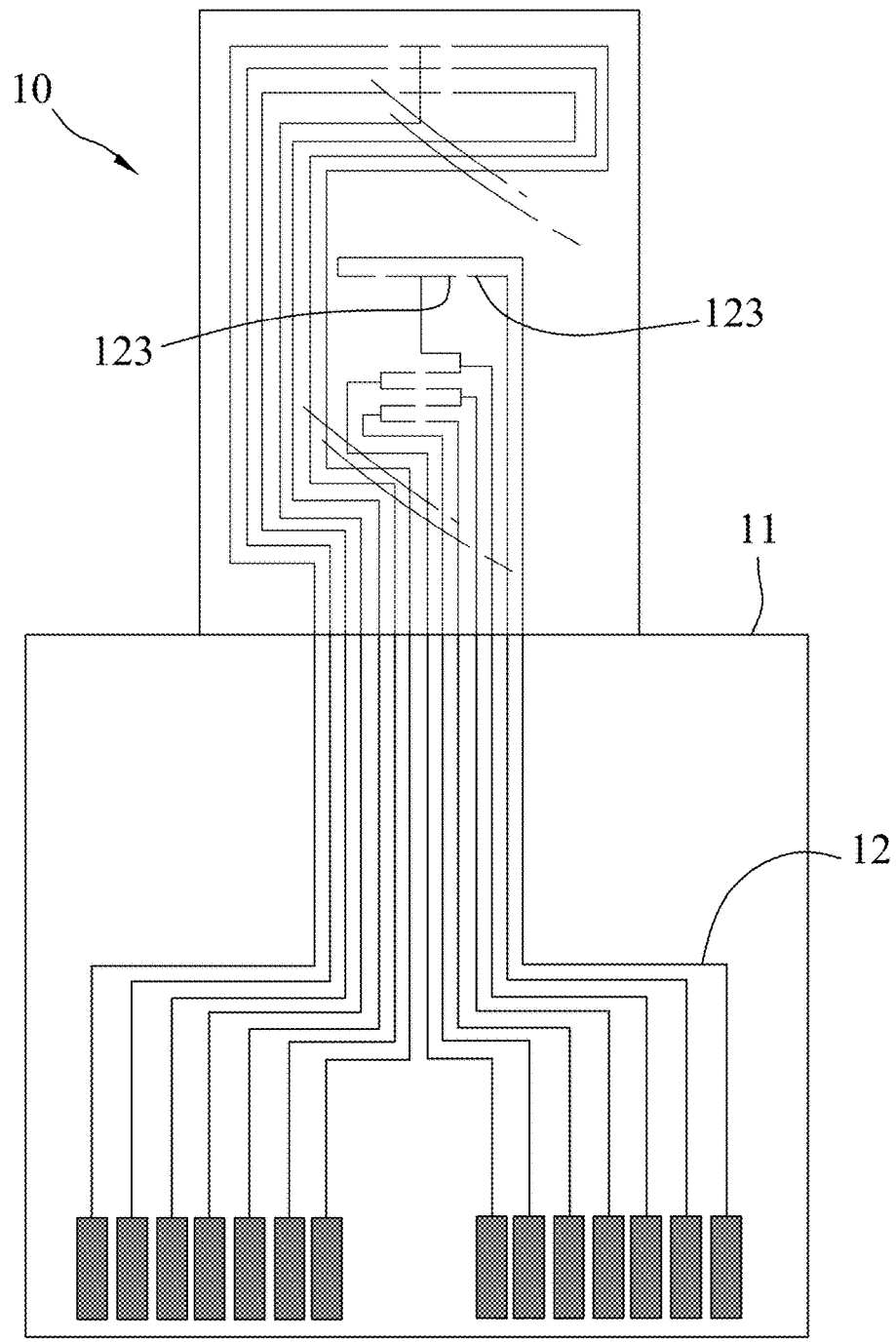
FIG. 1 is a top view of a first embodiment of a breath sensing tube according to this disclosure.

Before the disclosure is described in greater detail, it should be noted that like elements are denoted by the same reference numerals throughout the disclosure.

Figure 2:
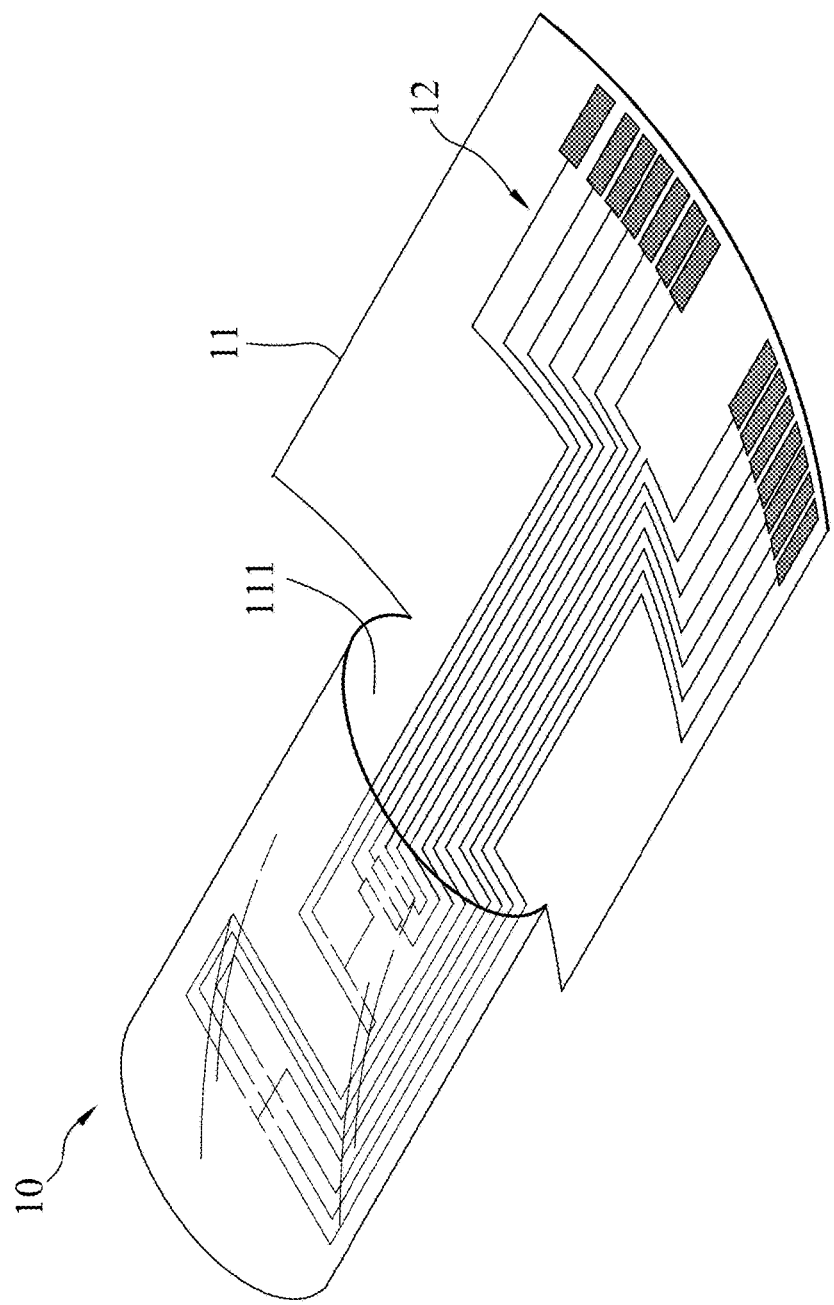
FIG. 2 is a schematic view of the first embodiment.
Figure 3:
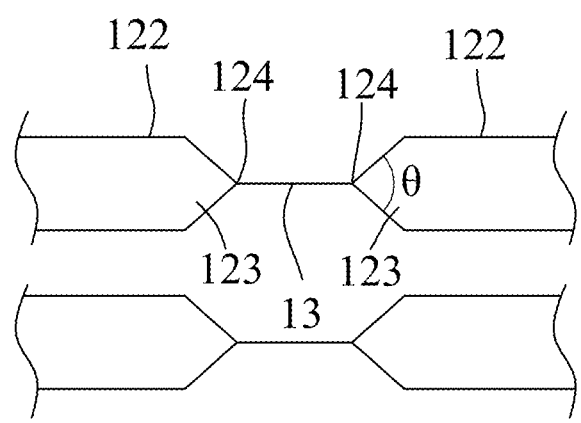
FIG. 3 is a partial schematic view of the first embodiment.

Referring to FIGS. 1 to 3, the first embodiment of a breath sensing tube 10 according to the disclosure includes a blowing body 11, a patterned circuit layer 12, and a single nanowire 13.

The blowing body 11 defines a blowing channel 111.

The patterned circuit layer 12 includes at least one pair of sensor electrodes 122 which are disposed in the blowing channel 111 and which are spaced apart from each other. Each of the sensor electrodes 122 has a tapered end portion 123 with a tip 124.

The single nanowire 13 interconnects the tips 124 of the tapered end portions 123.

Preferably, the blowing body 11 is made from a flexible material of an insulator. In the embodiment, the blowing body 11 is made from a flexible polymer. Each of the tapered end portions 123 defines an internal tip angle θ. The tapered end portions 123 are tapered toward each other. The patterned circuit layer 12 is made from Ti and Au.

Preferably, each of the tip angle θ ranges from 60 degrees to 120 degrees. In the embodiment, the tip angle θ is 90 degrees.

The single nanowire 13 is made from TiO$_2$ or Ag. In the embodiment, the spacing between the tips 124 is 20 μm.

When a testing breath gas which is exhaled by a tester flows into the blowing channel 111 and contacts the single nanowire 13, the electrical properties of the single nanowire 13 is changed in accordance with the contents of the testing breath gas.

The following description is provided to illustrate an embodiment of a method of making the breath sensing tube 10 of the first embodiment of the disclosure, and should not be construed as limiting the scope of the disclosure.

Figure 4:
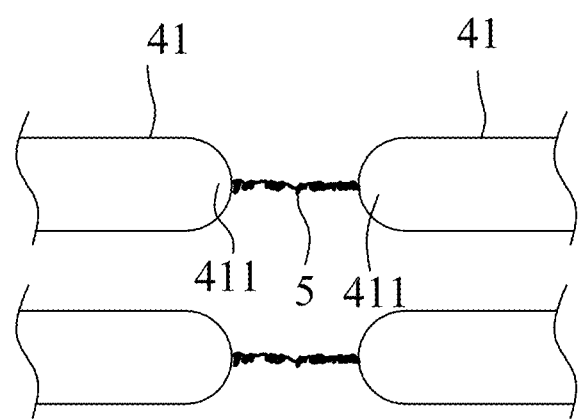
FIG. 4 is a partial schematic view of bath electrodes used in step (B) of a method of making the first embodiment of the breath sensing tube according to this disclosure.

The embodiment of the method of making the breath sensing tube 10 of the first embodiment of the disclosure includes the steps of: (A) dispersing a nanowire material in a solution in a dielectrophoretic bath, such that the nanowire material is formed into a plurality of individual nanowires and a plurality of nanowire aggregates 5 (shown in FIG. 4) in the solution in the dielectrophoretic bath; (B) adsorbing the nanowire aggregates 5 at least one of two bath electrodes 41 of the dielectrophoretic bath through dielectrophoresis so as to obtain a nanowire-containing solution containing the individual nanowires (see FIG. 4); (C) providing a substrate formed with at least one pair of the sensor electrodes 122 thereon; (D) contacting the sensor electrodes 122 with the nanowire-containing solution; and (E) subjecting the nanowire-containing solution to dielectrophoresis, so that one of the individual nanowires (i.e., the single nanowire 13) is adsorbed to the sensor electrodes 122 to interconnect the sensor electrodes 122.

Preferably, the method of making the breath sensing tube 10 of the embodiment further includes: rolling and shaping the substrate to form the blowing body 11 with the blowing channel 111 after step (E).

As mentioned above, the sensor electrodes 122 are disposed in the blowing channel 111, and are spaced apart from each other. Each of the sensor electrodes 122 includes the tapered end portion 123 with the tip 124, and the tip angle θ of the tapered end portion of each of the sensor electrodes ranges from 60 degrees to 120 degrees.

Preferably, each of the bath electrodes 41 of the dielectrophoretic bath includes an arc-shaped end portion 411. In certain embodiments, there are more than two pairs of bath electrodes 41 that are employed in the dielectrophoretic bath.

Preferably, the dielectrophoresis in step (E) is operated under a condition that the solution in the dielectrophoretic bath has a fluid-flow velocity of not smaller than 1 μL/min and not larger than 20 μL/min.

The nanowire material can be semiconductor or conductor. Preferably, the nanowire material can be made from TiO$_2$ or Ag.

Figure 5:
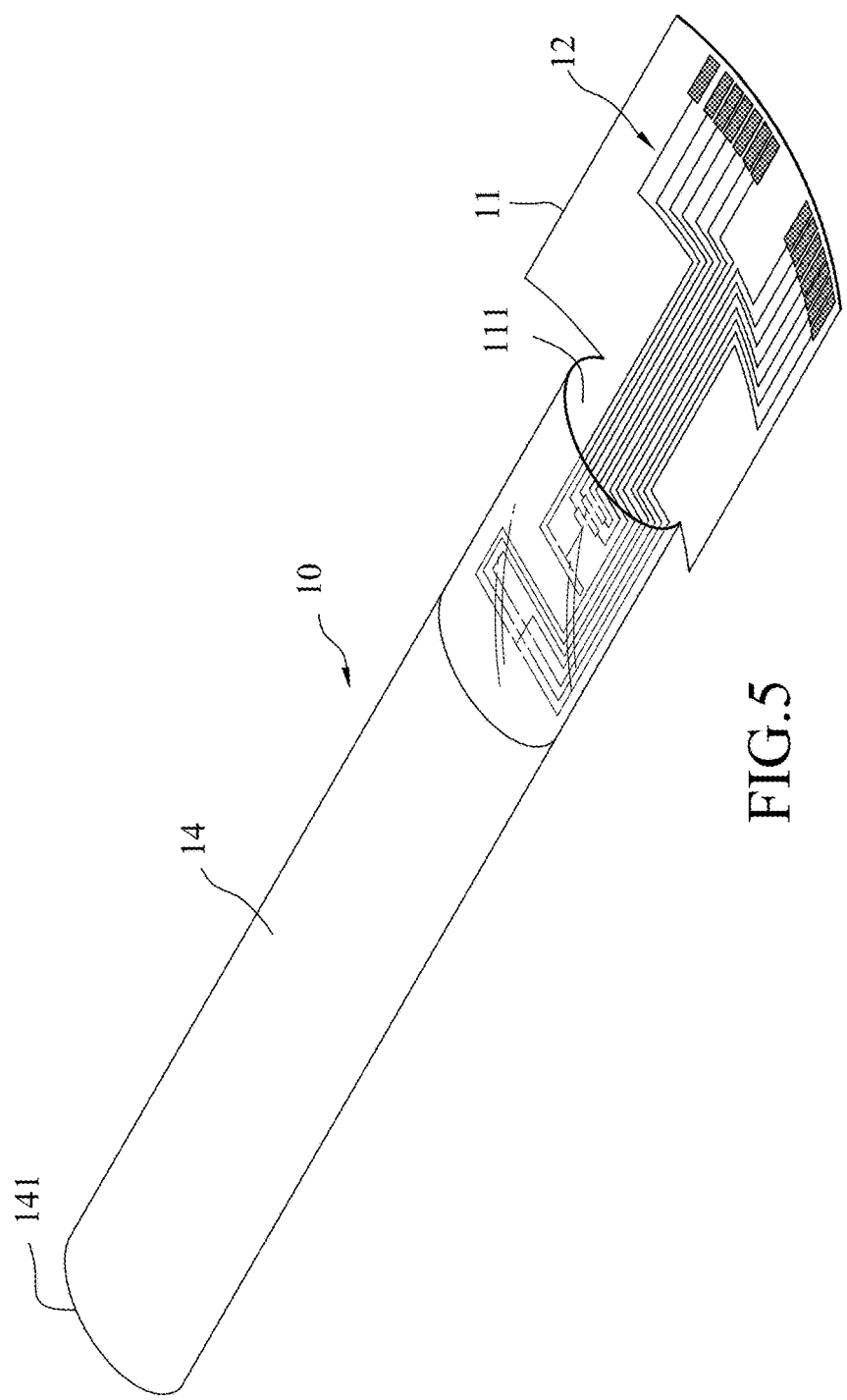
FIG. 5 is a schematic view of a second embodiment of a breath sensing tube according to this disclosure.

FIG. 5 illustrates the second embodiment of the breath sensing tube 10 of the disclosure. The second embodiment further includes an extension segment 14 as compared to the first embodiment. The extension segment 14 serves to reduce turbulence of a breath gas flow passing therethrough before the breath gas reaches the sensor electrodes 122. It is noted that the more turbulence, the less sensitivity of the breath sensing tube 10 will be.

The extension segment 14 defines an extending blowing channel 141 in fluid communication with the blowing channel 111 in the blowing body 11.

A minimum effective length ($L_e$) of the extension segment 14 for suppression of the turbulence (for a fluid flow velocity of 1-8 L/s) may be calculated based on the following equation:

$$\frac{Le}{D} \cong 4.4 \text{Re}^{1/6},$$

wherein D is a maximum diameter of the extension segment 14 and $R_e$ is the Reynolds number.

Table 1 shows the calculated minimum effective length ($L_e$) of the extension segment 14 for different expiratory flow velocities based on the parameters shown in Table 2.

TABLE 1

| | Expiratory flow velocity (L/s) | | | | | | | |
|---|---|---|---|---|---|---|---|---|
| | 1 | 2 | 3 | 4 | 5 | 6 | 7 | 8 |
| Minimum effective length ($L_e$) (cm) | 17.6 | 19.7 | 21.1 | 22.2 | 23 | 23.7 | 24.3 | 24.8 |

TABLE 2

| Maximum diameter (D) | Fluid density (ρ) | Dynamic viscosity coefficient (μ) |
|---|---|---|
| 1.91 cm | 1.15 kg/m$^3$ | 1.88 * 105 Ns/m$^2$ |

Figure 6:
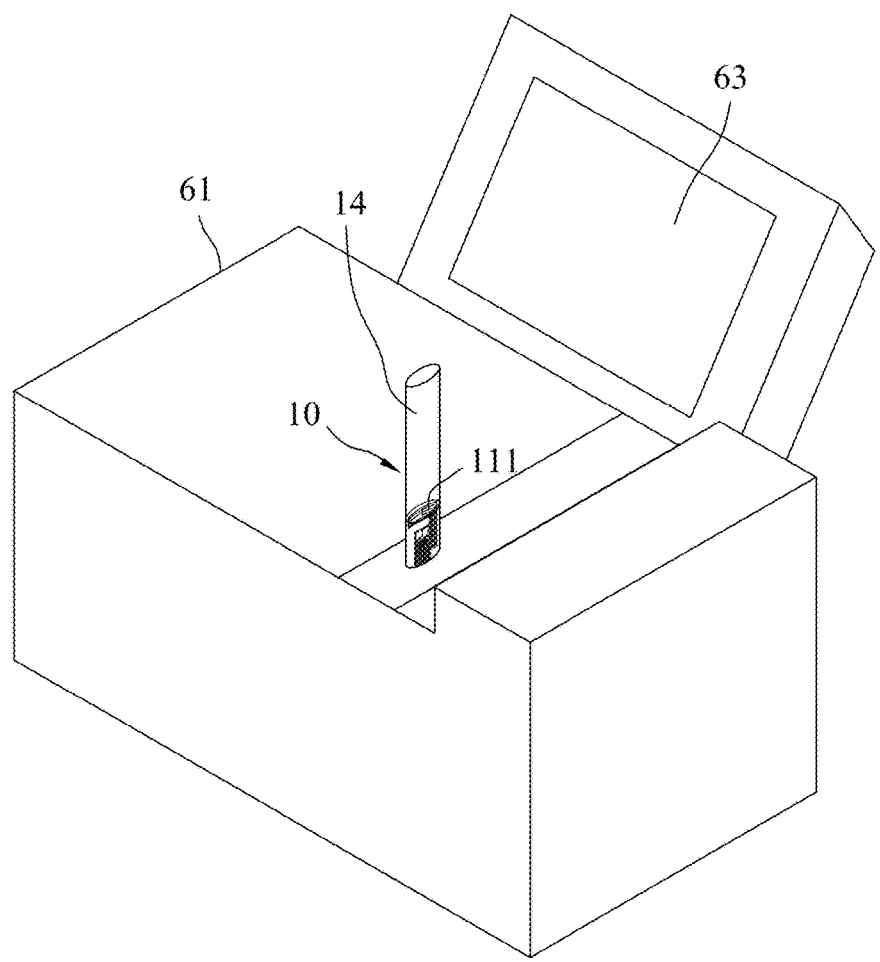
FIG. 6 is a schematic view of a sensing system with the breath sensing tube of the second embodiment according to this disclosure.
Figure 7:
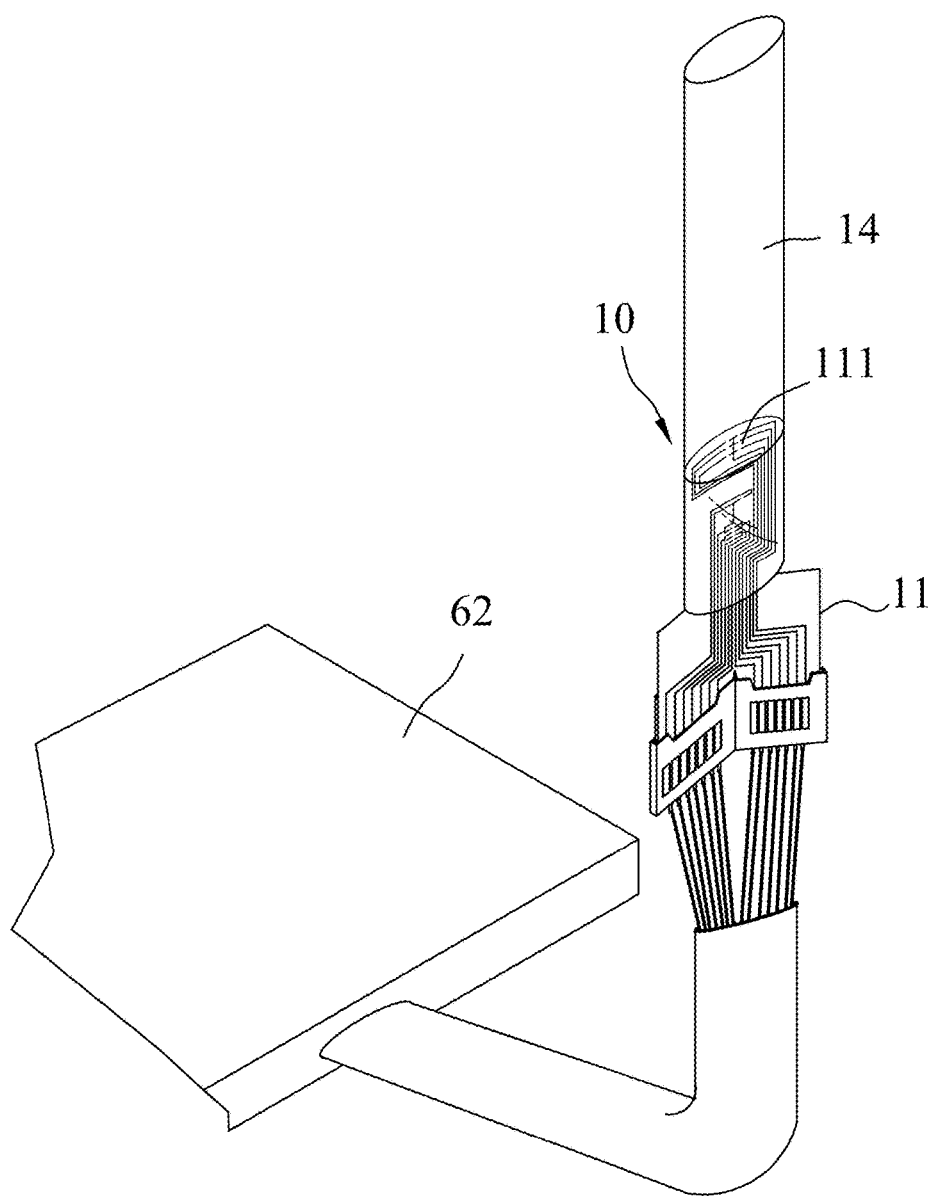
FIG. 7 is a partial perspective schematic view of the sensing system shown in FIG. 6, showing the breath sensing tube of the second embodiment and a circuit device.

FIGS. 6 and 7 illustrate an embodiment of a sensing system according to this disclosure. The embodiment of the sensing system includes a stage 61, the breath sensing tube 10 of the second embodiment, a circuit device 62, and a man-machine interface device 63.

The breath sensing tube 10 is disposed on the stage 61. The sensor electrodes 122 of the breath sensing tube 10 are electrically connected to the circuit device 62. In the embodiment, the breath sensing tube 10 is electrically connected to the circuit device 62 through an adaptor, such as an USB connector.

The circuit device 62 includes an embedded Platform (not shown), a regulator circuit (not shown), a UV LED controlling circuit (not shown), a bridge sensing circuit (not shown), a charge and discharge protection circuit (not shown), and an analog to digital converter (not shown).

In certain embodiments of the sensing system, the embedded Platform may be a product with a catalog number 6410L, available from DMATEK.

The regulator circuit is a regulator IC chip (LM317, available from STMicroelectronics, Inc., and is configured to allocate a 5 V power source. The bridge sensing circuit uses the Wheatstone bridge to amplify an analog signal produced from the resistance variation of the single nanowire 13.

The analog to digital converter receives and converts the analog signal from the bridge sensing circuit into a digital signal, and then transfers the digital signal to the embedded Platform to obtain data corresponding to physical properties, such as flow velocity, temperature, and humidity.

The man-machine interface device 63 couples the circuit device 62 to display the data generated from the embedded Platform. The man-machine interface device 63 further includes a button (not shown) to control the UV LED controlling circuit.

When the testing breath gas flows into the blowing channel 111 and contacts the single nanowire 13, the circuit device 62 receives the signal corresponding to the resistance variation of the single nanowire 13 from the breath sensing tube, and the man-machine interface device 63 displays the information of the signal.

Figure 8:
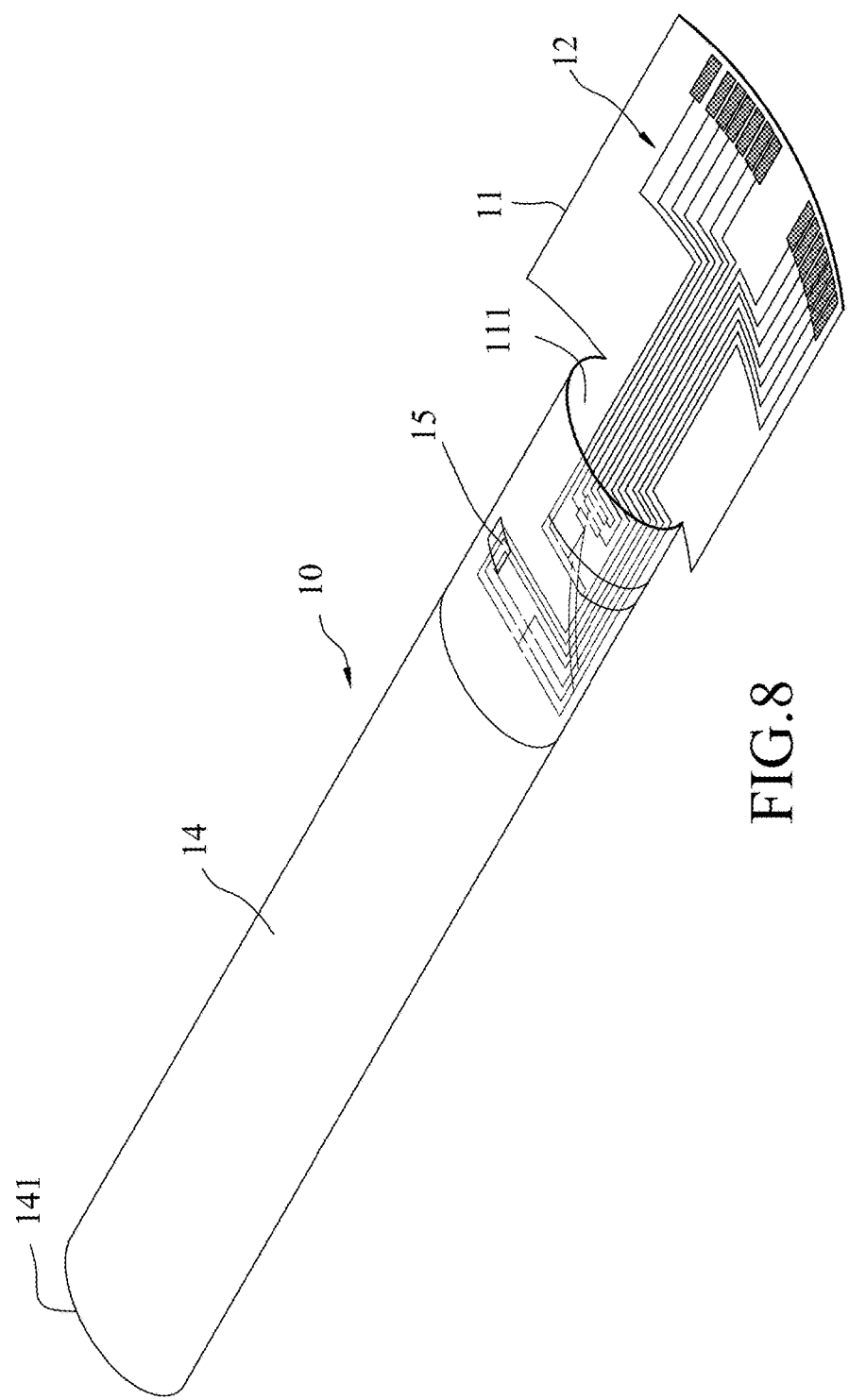
FIG. 8 is a top view of a third embodiment of a breath sensing tube according to this disclosure.

FIG. 8 illustrates the third embodiment of the breath sensing tube 10 of the disclosure. The breath sensing tube 10 further includes a UV light transparent film 15 which can be made from polydimethylsiloxane (PDMS) or cycloolefin copolymer (COC) and which is disposed on the single nanowire 13 and connected to the blowing body 11. It is noted that when the single nanowire 13 is made from $TiO_2$, the single nanowire 13 may be irradiated with UV-emitting light. When the UV-emitting light energy is larger than the band gap of $TiO_2$ between the conduction band and the valence band, the resistance of the single nanowire 13 may be reduced.

Figure 9:
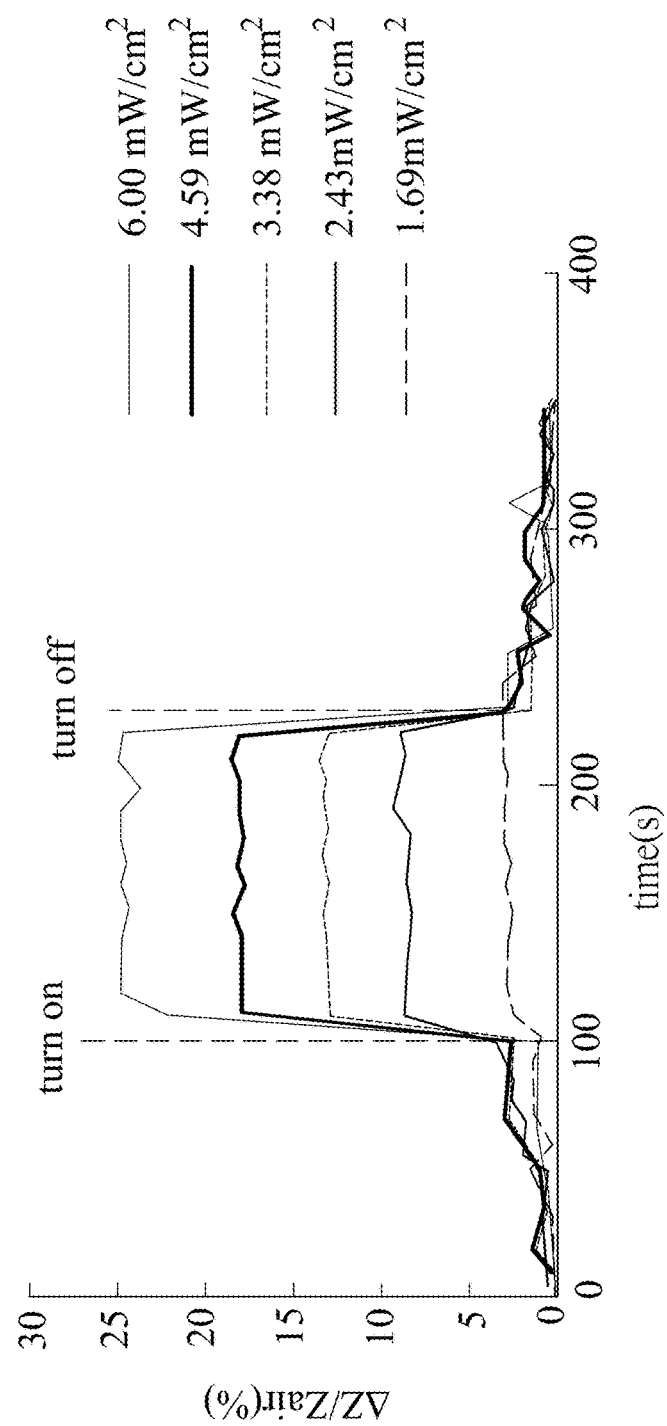
FIG. 9 is a plot illustrating time vs. unit resistance variation of a nanowire at different UV-emitting light energy under an operating voltage of 1V.

FIG. 9 is a plot of time vs. unit resistance variation of the breath sensing tube 10 for different pulsed output power densities of a UV-emitting light source applied to the sensing tube 10. $\Delta Z$ is a resistance variation between a resistance of the single nanowire at an elapsed time (the time the UV-emitting light source is turned off) and an initial resistance Z of the single nanowire at an initial time (the time the UV-emitting light source is turned on). The results show that the unit resistance variation of the breath sensing tube can be raised using a higher output power density of the UV-emitting light energy.

<Analysis data>

Figure 10:
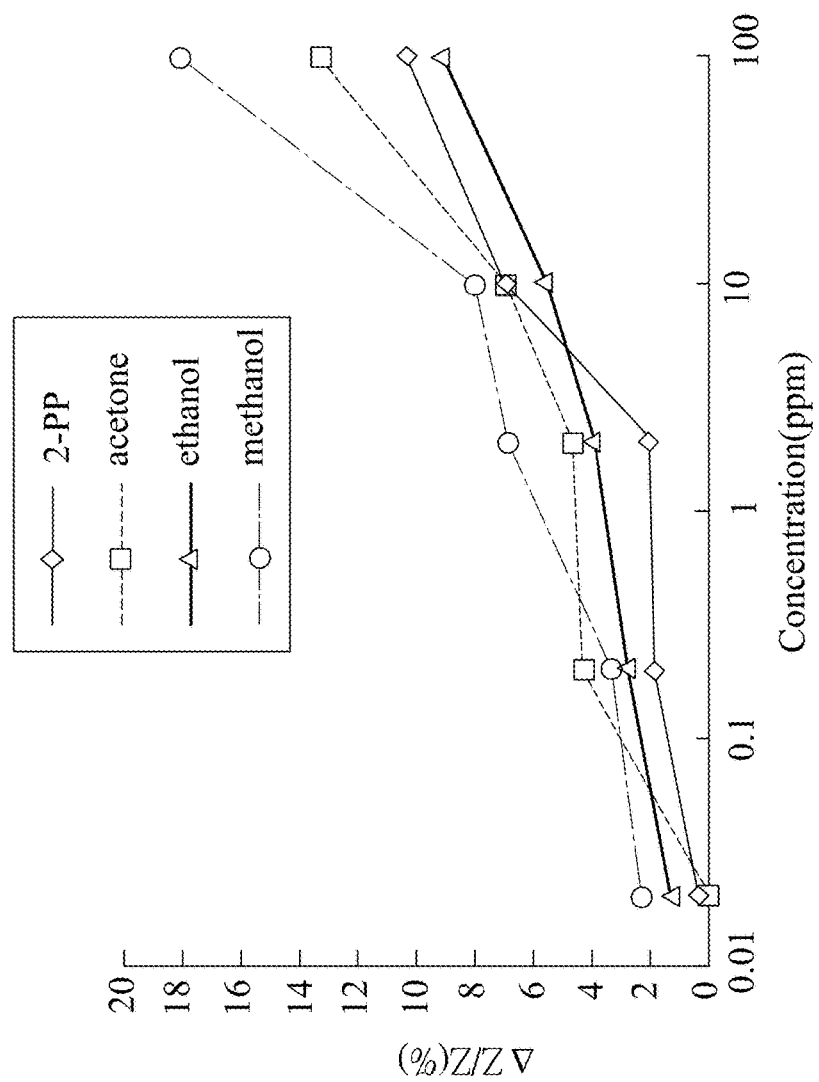
FIG. 10 is a plot illustrating a concentration of a testing gas vs. unit resistance variation of the nanowire for different testing gases.

FIG. 10 is a plot of concentration vs. unit resistance variation for different testing gases. The measurement was conducted under the following conditions: the single nanowire was made from $TiO_2$ and was irradiated with UV light (6 mW/cm$^2$). $\Delta Z$ is a resistance variation between a resistance of the single nanowire exposed to the testing gas and an initial resistance Z of the single nanowire exposed to air. The testing gases for the measurement are 2PP (2wo-propyl-1-pentanol), acetone, ethanol, and methanol. The results show that the resistance variation ($\Delta Z$) of the single nanowire may be increased with an increase of the concentration of the testing gas.

Figure 11:
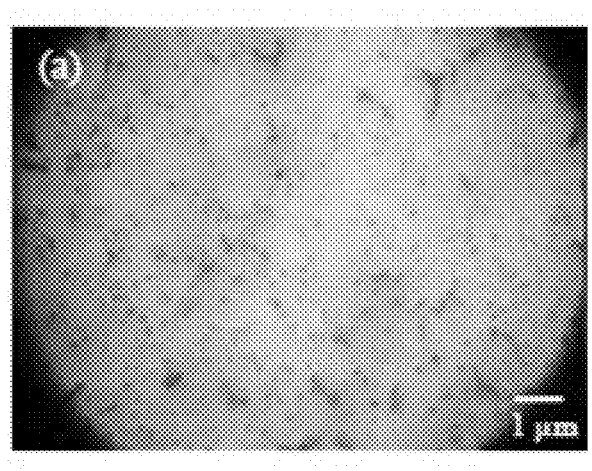
FIG. 11 is a view illustrating a state of the solution in the dielectrophoretic bath.
Figure 12:
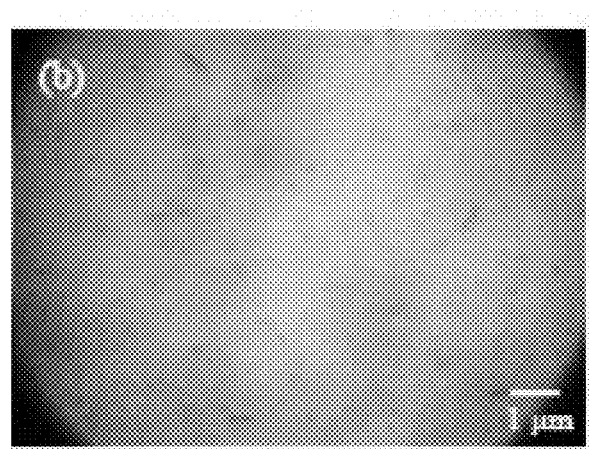
FIG. 12 is a view illustrating another state of the solution in the dielectrophoretic bath.

FIG. 11 illustrates a state of the solution in the dielectrophoretic bath in step (A), in which the nanowire material is placed into the solution in the dielectrophoretic bath before the dielectrophoresis is initiated. FIG. 12 illustrates another state of the solution in the dielectrophoretic bath in step (B), in which the nanowire aggregates 5 are absorbed on the bath electrodes 41 after the dielectrophoresis is completed.

Figure 13:
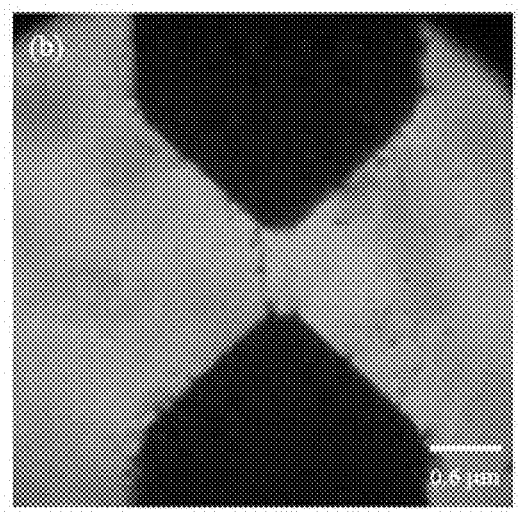
FIG. 13 is a view illustrating a configuration of an assembly of sensor electrodes and a single nanowire interconnecting the sensor electrodes.
Figure 14:
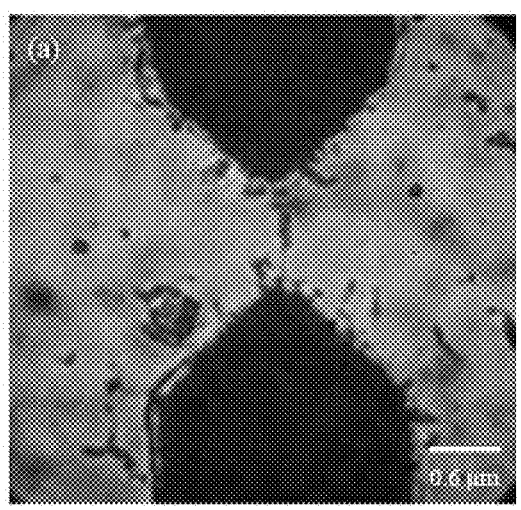
FIG. 14 is a view illustrating a configuration of an assembly of sensor electrodes and nanowire aggregates attached to the sensor electrodes.

FIG. 13 illustrates the configuration of an assembly of the sensor electrodes 122 and the single nanowire interconnecting the sensor electrodes 122. The assembly was formed by the method of the disclosure. As a comparison, FIG. 14 illustrates the configuration of an assembly of the sensor electrodes and nanowire aggregates attached to the sensor electrodes. The assembly of FIG. 14 was formed by a method similar to that of the disclosure, except that step (B) was skipped.

Figure 15:
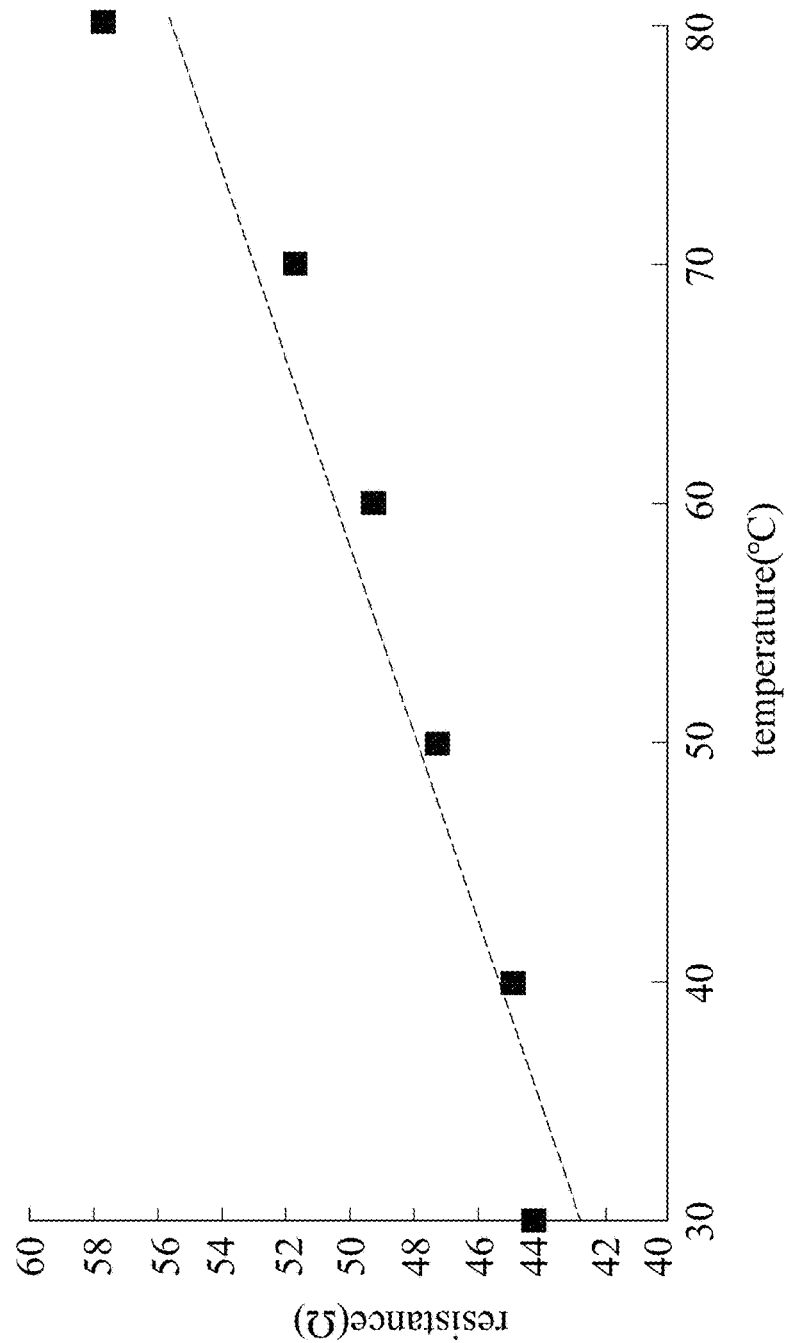
FIG. 15 is a plot illustrating temperature vs. a resistance of the nanowire.

FIG. 15 is a plot of temperature vs. resistance of the single nanowire made from Ag of the sensing system. The resistance of the single nanowire is 40 Ω under room temperature. As shown in FIG. 15, the higher the temperature, the larger the resistance of the single nanowire will be.

Figure 16:
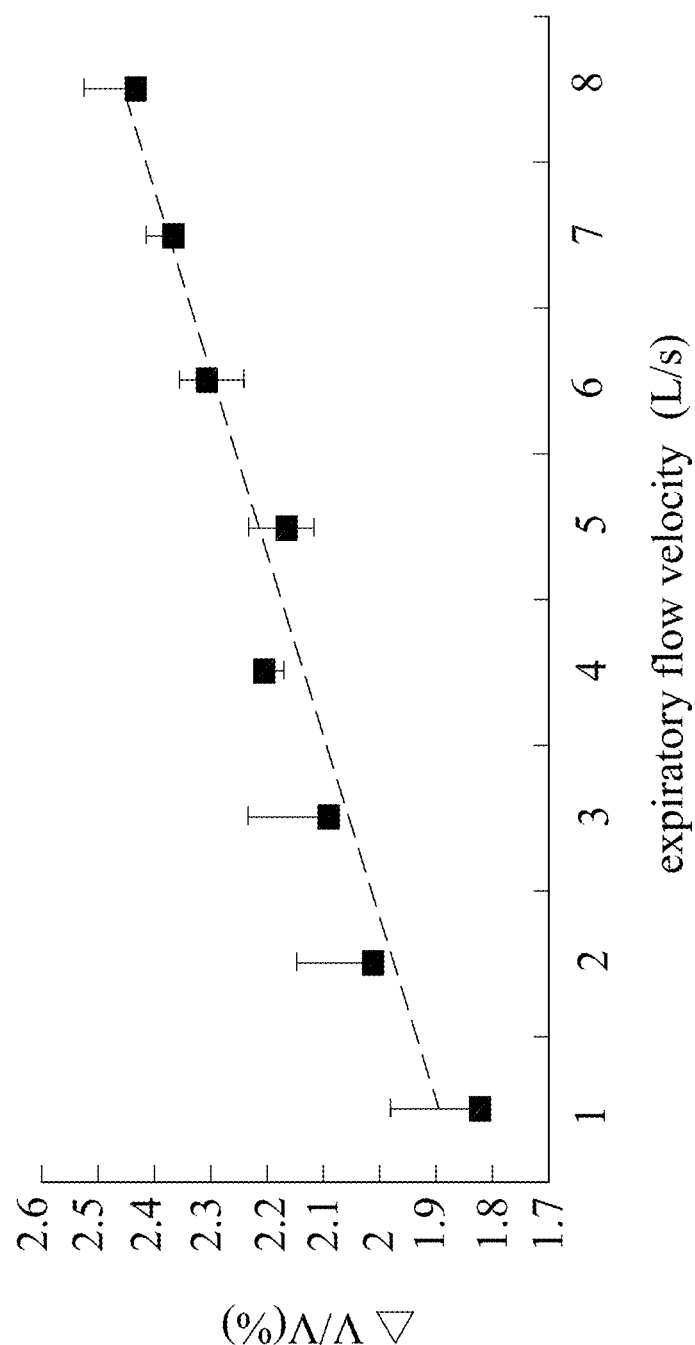
FIG. 16 is a plot illustrating expiratory flow velocity vs. voltage variation of an external energy.

FIG. 16 is a plot of flow velocity of an air flow vs. unit voltage variation for the sensing system including a single nanowire made from Ag. The measurement was conducted as follows. The single nanowire was first heated to a predetermined temperature using an external power. The air flow was introduced into the sensing system, and absorbed heat from the heated single nanowire while passing therethrough, which caused a decrease in the temperature of the single nanowire. The external power serves to apply a compensate voltage to compensate a temperature drop of the single nanowire due to the exposure to the air flow so as to maintain the single nanowire at the predetermined temperature. $\Delta V$ is a voltage variation between the compensate voltage applied by the external power to the single nanowire under a flow velocity of the air flow and an initial voltage V applied to single nanowire under zero flow velocity. The larger the flow velocity of the air flow, the larger the temperature drop of the single nanowire will be and the higher the compensate voltage will be needed for compensating the energy loss of the single nanowire.

Figure 17:
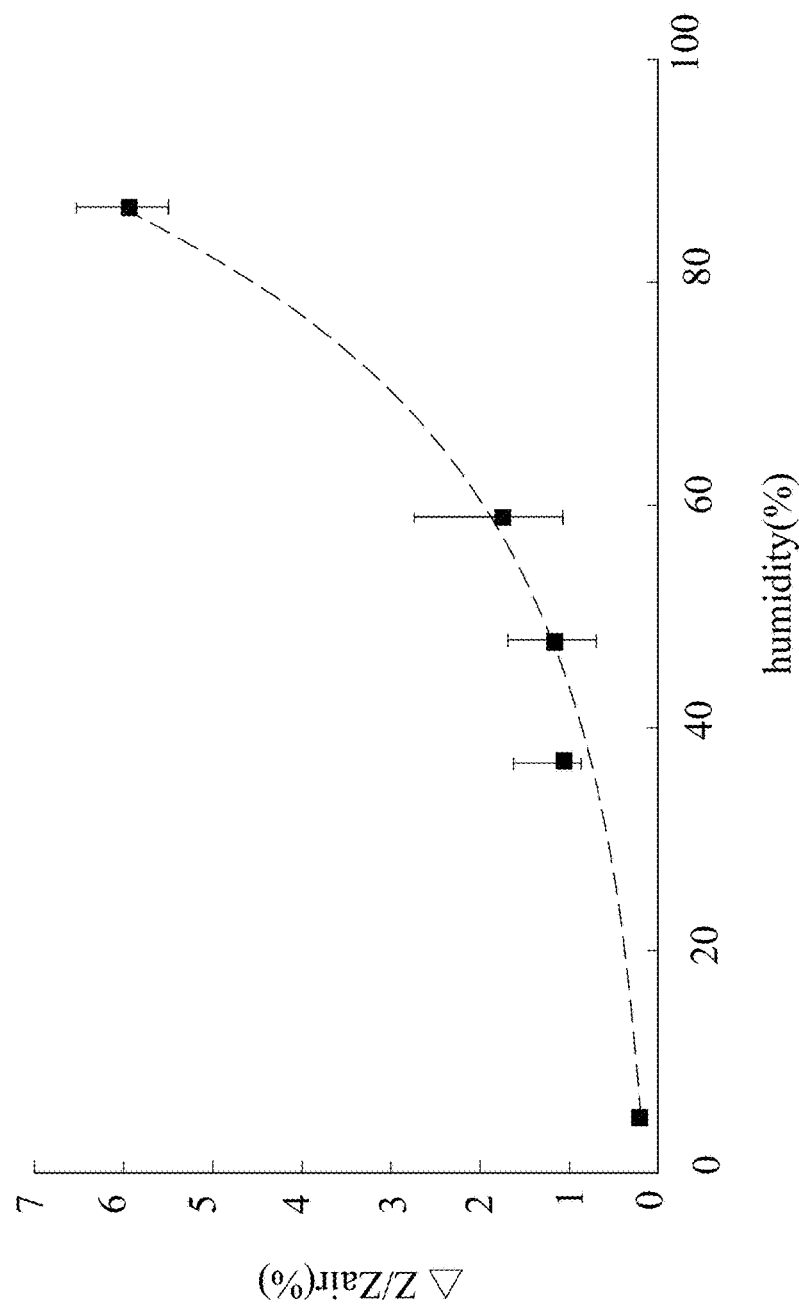
FIG. 17 is a plot illustrating humidity vs. unit resistance variation of the nanowire.

FIG. 17 is a plot of humidity vs. unit resistance variation of the single nanowire (made from $TiO_2$) of the sensing system. $\Delta Z$ is a resistance variation between a resistance of the single nanowire under a humidity in an air environment and an initial resistance $Z_{air}$ of the single nanowire under a humidity of substantially zero in the air environment. The larger the humidity, the higher the resistance variation of the single nanowire will be.

Figure 18:
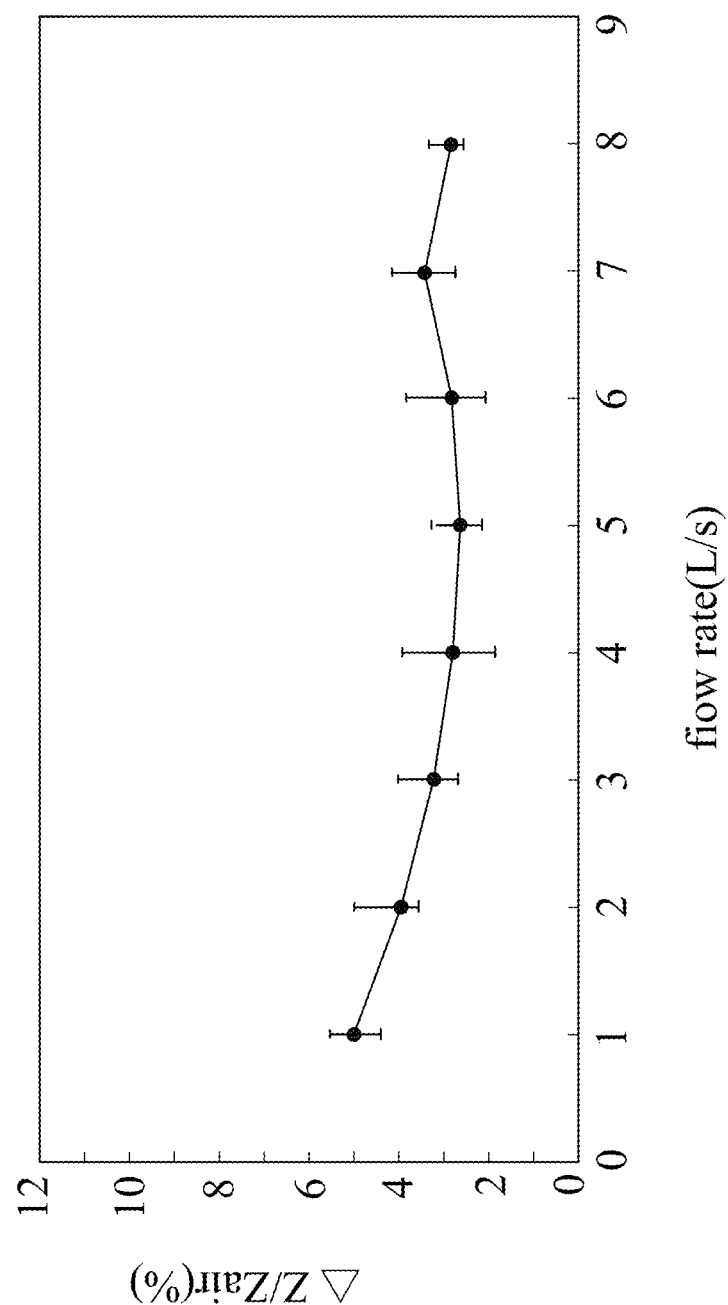
FIG. 18 is a plot illustrating flow rate vs. unit resistance variation of the nanowire.

FIG. 18 is plot of expiratory flow velocity of a testing breath gas vs. unit resistance variation of a single nanowire of the sensing system. The measurement was conducted under conditions similar to those of FIG. 16, except that the air flow of this measurement contained a small amount of 2-PP. The testing gas contains 100 ppb concentration of 2-PP which is used as a lung cancer marker.

Figure 19:
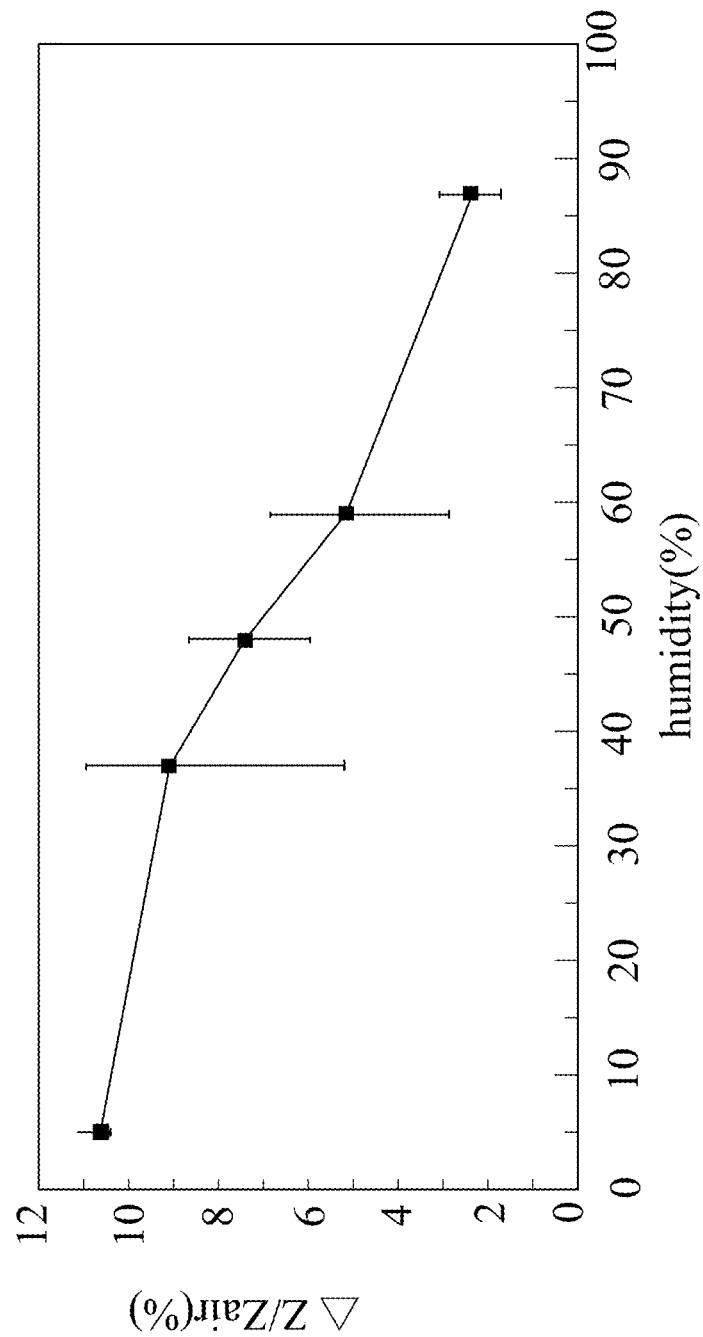
FIG. 19 is a plot illustrating humidity vs. unit resistance variation of the nanowire.

FIG. 19 is plot of humidity of a testing gas vs. unit resistance variation of the nanowire of the sensing system. The measurement was conducted under conditions similar to those of FIG. 17, except that the air environment contained 100 ppb concentration of 2-PP.

With the breath sensing tube 10 made by the method of the present disclosure, the aforesaid drawbacks associated with the prior art can be alleviated.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method of making a breath sensing tube, comprising:
   (A) dispersing a nanowire material in a solution in a dielectrophoretic bath, such that the nanowire material is formed into a plurality of individual nanowires and a plurality of nanowire aggregates in the solution in the dielectrophoretic bath;
   (B) adsorbing the nanowire aggregates on a bath electrode of the dielectrophoretic bath through dielectrophoresis so as to obtain a nanowire-containing solution containing the individual nanowires;
   (C) providing a substrate formed with at least one pair of sensor electrodes thereon;
   (D) contacting the sensor electrodes with the nanowire-containing solution;

(E) subjecting the nanowire-containing solution to dielectrophoresis, so that one of the individual nanowires is adsorbed to the sensor electrodes to interconnect the sensor electrodes; and (F) rolling and shaping the substrate to form a blowing body defining a blowing channel after step (E).

2. The method of claim 1, wherein the sensor electrodes are disposed in the blowing channel and are spaced apart from each other, each of the sensor electrodes including a tapered end portion with a tip.

3. The method of claim 2, wherein the tapered end portion of each of the sensor electrodes defines a tip angle, the tip angle ranging from 60 degrees to 120 degrees.

4. The method of claim 1, wherein the bath electrode of the dielectrophoretic bath includes an arc-shaped end portion.

5. The method of claim 1, wherein the nanowire material is made from $TiO_2$ or Ag.

6. The method of claim 1, wherein the dielectrophoresis in step (E) is operated under a condition that nanowire-containing solution has a fluid-flow velocity of not smaller than 1 μL/min and not larger than 20 μL/min.

* * * * *